(12) United States Patent
Humbert et al.

(10) Patent No.: US 8,963,563 B2
(45) Date of Patent: Feb. 24, 2015

(54) CAPACITIVE SENSOR FOR DETECTING THE PRESENCE OF A SUBSTANCE

(75) Inventors: Aurelie Humbert, Brussels (BE); Matthias Merz, Leuven (BE); Youri Victorovitch Ponomarev, Leuven (NL); Roel Daamen, Herkenbosch (NL); Marcus Johannes Henricus van Dal, Heverlee (BE)

(73) Assignee: NXP B.V., Eindhoven (NL)

( * ) Notice: Subject to any disclaimer, the term of this patent is extended or adjusted under 35 U.S.C. 154(b) by 761 days.

(21) Appl. No.: 12/969,884

(22) Filed: Dec. 16, 2010

(65) Prior Publication Data

US 2011/0146400 A1   Jun. 23, 2011

(30) Foreign Application Priority Data

Dec. 16, 2009   (EP) ..................................... 09179409

(51) Int. Cl.
*G01N 27/22*   (2006.01)
*G01R 27/26*   (2006.01)

(52) U.S. Cl.
CPC .......... *G01N 27/223* (2013.01); *G01R 27/2605* (2013.01)
USPC .......................................... 324/658; 324/694

(58) Field of Classification Search
CPC .......................... G01R 27/2605; G01N 27/223
USPC ........................................................ 324/658
See application file for complete search history.

(56) References Cited

U.S. PATENT DOCUMENTS

| | | | |
|---|---|---|---|
| 4,429,343 A | 1/1984 | Freud | |
| 6,222,376 B1 | 4/2001 | Tenney | |
| 6,525,547 B2 * | 2/2003 | Hayes | 324/662 |
| 6,690,569 B1 | 2/2004 | Mayer et al. | |
| 7,222,531 B2 | 5/2007 | Isogai et al. | |
| 2002/0109959 A1 | 8/2002 | Toyoda et al. | |
| 2002/0136664 A1 | 9/2002 | Lee et al. | |
| 2004/0160233 A1 * | 8/2004 | Forster | 324/667 |
| 2006/0105449 A1 | 5/2006 | Larmer et al. | |
| 2006/0132148 A1 * | 6/2006 | Cheah et al. | 324/671 |
| 2007/0186649 A1 | 8/2007 | Sudo | |
| 2009/0141767 A1 | 6/2009 | Cummins | |
| 2009/0160460 A1 * | 6/2009 | Harish | 324/674 |
| 2010/0085322 A1 * | 4/2010 | Mamba et al. | 345/173 |

FOREIGN PATENT DOCUMENTS

| | | |
|---|---|---|
| CN | 1021431 A | 10/1988 |
| CN | 1343308 A | 4/2002 |
| CN | 101310175 A | 11/2008 |
| CN | 101398402 A | 4/2009 |
| EP | 2343541 A1 | 7/2011 |
| WO | 2007/057794 A1 | 5/2009 |
| WO | 2009/066992 A2 | 5/2009 |

* cited by examiner

OTHER PUBLICATIONS

Extended European Search Report for Patent Appln. No. 09179409.9 (Jun. 2, 2010).

*Primary Examiner* — Jeff Natalini (57) ABSTRACT

A capacitive sensor for detecting the presence of a substance includes a plurality of upstanding conductive pillars arranged within a first layer of the sensor, a first electrode connected to a first group of the pillars, a second electrode connected to a second, different group of the pillars, and a dielectric material arranged adjacent the pillars, for altering the capacitance of the sensor in response to the presence of said substance.

20 Claims, 8 Drawing Sheets

CAPACITIVE SENSOR FOR DETECTING THE PRESENCE OF A SUBSTANCE

This application claims the priority under 35 U.S.C. §119 of European patent application no. 09179409.9, filed on Dec. 16, 2009, the contents of which are incorporated by reference herein.

This invention relates to a capacitive sensor.

Capacitive sensors are known in the art, for detecting the presence of substances such as humidity, gases or other fluids. Two known types of capacitive sensors are shown in FIGS. 1 and 2.

Figure 1:
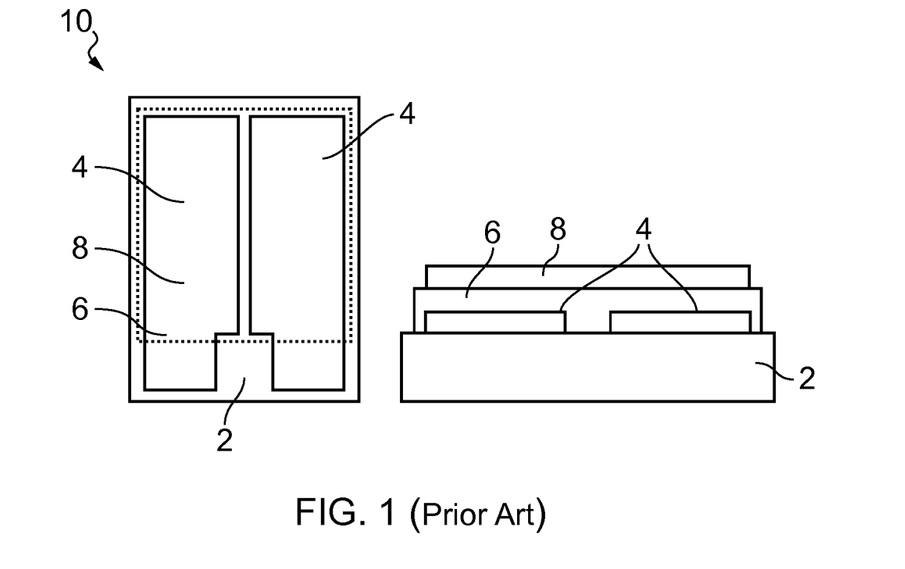
FIG. 1 shows a known kind of capacitive sensor.

The capacitive humidity sensor 10 in FIG. 1 includes a pair of electrodes 4 on a substrate 2. The electrodes 4 act as capacitor plates, and are covered by a humidity sensitive material 6 and a gold layer 8. The humidity sensitive material 6 separates the two electrodes 4, and has a variable dielectric constant. In particular, the dielectric constant of the humidity sensitive material 6 varies in response to exposure to water vapour. By measuring the capacitance of the two electrodes 4 of the sensor 10, it is therefore possible to detect the presence of water vapour, and also to make some kind of determination as to the humidity of the surrounding environment.

Figure 2:
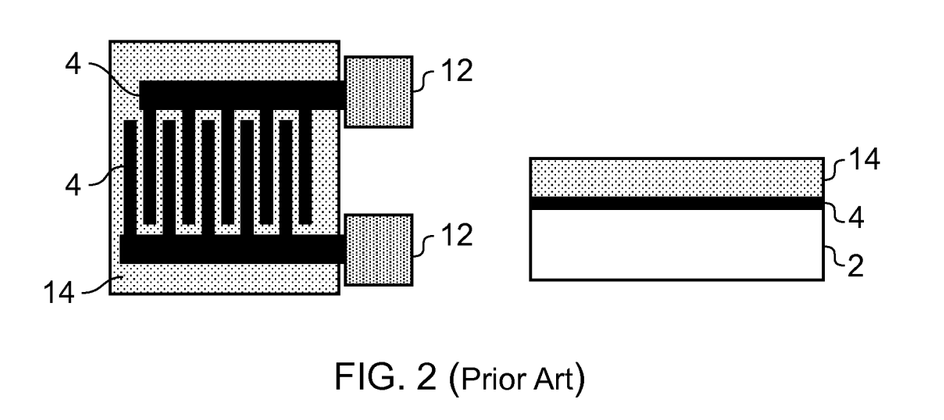
FIG. 2 shows another known kind of capacitive sensor.

The capacitive humidity sensor 10 shown in FIG. 2 operates in a similar fashion to that described above in relation to FIG. 1. The sensor 10 includes two electrodes 4, which again act as capacitor plates. The electrodes 4 comprise metal tracks laid down on the surface of a substrate 2 (such as a semiconductor substrate), and are proved with connection pads 12. As in FIG. 1, the electrodes 4 are covered with a humidity sensitive material 14, which has a dielectric constant that varies in response to the presence of water vapour.

In the sensor 10 of FIG. 2, the electrodes 4 adopt a so-called meander pattern, to increase their surface area. In particular, the electrodes 4 are patterned in the shape of a plurality of interdigitated fingers, to increase their surface area overlap. These features increase the sensitivity of the sensor 10, allowing it to measure smaller levels of humidity.

Although the sensitivity of the sensor 10 in FIG. 2 improves upon the sensitivity of the device shown in FIG. 1, it is nevertheless still generally desirable, in the field of capacitive sensors, to provide devices with even greater sensitivities.

SUMMARY OF THE INVENTION

Aspects of the invention are set out in the accompanying independent and dependent claims. Combinations of features from the dependent claims may be combined with features of the independent claims as appropriate and not merely as explicitly set out in the claims.

According to an aspect of the invention, there is provided a capacitive sensor for detecting the presence of a substance, the sensor comprising:
- a plurality of upstanding conductive pillars arranged within a first layer of the sensor;
- a first electrode connected to a first group of said pillars;
- a second electrode connected to a second, different group of said pillars; and
- a dielectric material for altering the capacitance of the first and second groups of pillars in response to the presence of said substance.

The provision of upstanding conductive pillars acting as capacitor plates in accordance with embodiments of this invention allows the sensitivity of the sensor to be accurately tailored to application requirements. By way of example, the distribution and spacing of the pillars in the first layer of the sensor can be precisely determined to meet application requirements, in a manner not possible using sensor designs of the kind shown in FIGS. 1 and 2.

In one embodiment, the conductive pillars can comprise a plurality of vias in a semiconductor substrate, filled with a conductive material such as Tungsten. The manufacture of vias of this kind is a well established process and, as such, a capacitive sensor according to this embodiment can be manufactured using standard semiconductor processing steps. Accordingly, a sensor according to an embodiment of the invention can be readily integrated into existing IC manufacture processes, without the need for the introduction or development of new and unusual process steps, and without the need for the use of additional masks.

It is envisaged that the dielectric material could be located between the conductive pillars in the first layer. However, the dielectric material may also be provided in a second, separate layer. The second layer may be adjacent (above or below) the first layer. In such embodiments, a further dielectric material (such as an oxide) can be located between the pillars in the first layer. This allows a straight forward process to be used in the manufacture of the sensor, in which the first layer containing the conductive pillars can be easily planarised (using, for example, a CMP step), prior to the addition of the dielectric layer.

The first and second electrodes connect to the pillars, to define the first and second groups. These electrodes can take on a number of different configurations. For example, the electrodes may be provided in a common layer, and given a pattern that defines the two groups. Alternatively, the electrodes may be occupy separate layers in the sensor, which eases the degree of patterning that is required (for example, the electrodes may overlap to some degree).

As indicated above, the distribution of the conductive pillars can be chosen in accordance with application requirements.

In one example distribution, the first group and the second group of pillars are arranged in rows. The rows can be alternating rows. For example, the rows can be interdigitated. In one embodiment, the pillars in each row can be offset with respect the pillars in adjacent rows, allowing the sensitivity of the device to be adjusted.

In another example distribution, the pillars can be arranged in a regular array of tessellating polygons, with a pillar from the second group located at the corners of each polygon, and with at least one pillar of the first group located toward the centre of each polygon. By surrounding the pillars of the first group with pillars of the second group, the sensitivity of the sensor can be maximised. The regular array may, for example, be a hexagonal array or a rectangular array. A hexagonal array would allow the highest packing density of pillars in the first layer.

In some example distributions, the nearest neighbours of the pillars in the first group can each comprise pillars in the second group. The next nearest neighbours of the pillars in the first group can also each comprise pillars in the second group.

The dielectric material for altering the capacitance of the first and second groups of pillars can be chosen according to application requirements. By way of example only, in the food packaging industry, it is useful to be able to determine the condition of food in a container, by detecting the presence of substances such as $H_2O$ (humidity), $CO_2$, $O_2$, ethylene and $NH_3$. By selecting an appropriate dielectric, a sensor in accordance with an embodiment of the invention may be tailored for detecting one or more of these substances. Appropriate dielectrics will be known to the person skilled in the art.

According to another aspect of the invention, there is provided a radio frequency identification (RFID) tag comprising a sensor of the kind described above.

BRIEF DESCRIPTION OF THE DRAWINGS

Embodiments of the present invention will be described hereinafter, by way of example only, with reference to the accompanying drawings in which like reference signs relate to like elements and in which.

DETAILED DESCRIPTION

Embodiments of the present invention are described in the following with reference to the accompanying drawings.

Figure 3:
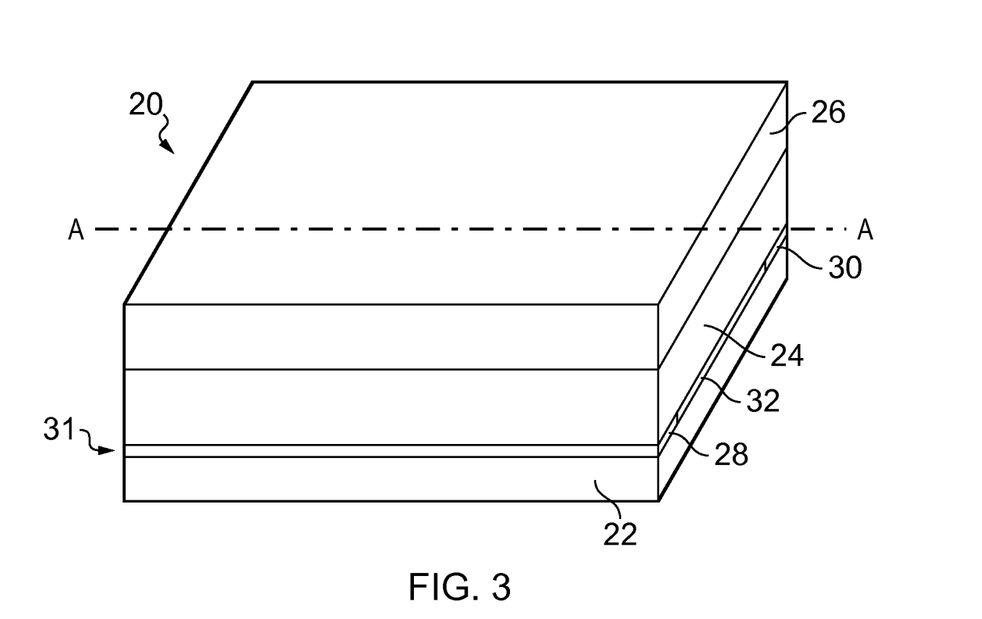
FIGS. 3-7 schematically illustrate a capacitive sensor according to an embodiment of the invention.

A first example of an embodiment of the invention is shown in FIGS. 3-7. In this example, a capacitive sensor 20 is constructed as a series of layers in a semiconductor substrate 22. As shown in FIG. 3, these layers in include a pillar layer 24. The pillar layer 24 comprises a layer of dielectric in which a plurality of conductive pillars are distributed. The arrangement of the pillars in the pillar layer 24 is described below in relation FIGS. 4 to 7.

The layers in the sensor 20 also include an electrode layer 31, which has a first electrode 28, a second electrode 30 and dielectric 32, which separates the first electrode 28 from the second electrode 30. As described in more detail below, the first electrode 28 and the second electrode 30 each connect to respective groups of conductive pillars which are provided in a pillar layer 24 of the sensor 20. The pillar layer in this example is positioned adjacent the electrode layer 31.

As also shown in FIG. 3, the sensor 20 further includes a dielectric layer 26, which is sensitive to the presence of a substance that is to be detected by the sensor 20. In particular, the dielectric layer 26, which is provided in close proximity to the electrically conducted pillars provided in the adjacent pillar layer 24, is configured to alter the capacitance of the first and second groups of pillars in the pillar layer in response to the presence of the substance to be detected. In this way, by measuring the capacitance of the first and second groups of pillars in the pillar layer 24, the presence of the substance to be detected can be determined, and also an estimate can be made as to the quantity or concentration of the substance that is present.

The mechanism by which the dielectric material alters the capacitance of the first and second groups of pillars in the pillar layer 24 typically involves the diffusion of the substance into the dielectric layer 26, thereby altering the dielectric constant of the dielectric layer 26. Since the dielectric layer is provided in close proximity to the electrically conductive pillars in the pillar layer 24, the change in dielectric constant in the dielectric layer 26 in turn results in a change in capacitance between the groups of conductive pillars. The use of dielectric materials having variable dielectric constants in the presence of substances to be detected is generally known in the art, and will not be elaborated upon further herein. As indicated above however, the actual material used in the dielectric layer 26 can be chosen according to the substance to be detected. Table 1 indicates a number of substances that can be detected in accordance with embodiments of this invention, and a number of alternative types of material that can be used in the dielectric layer 26 to detect those substances.

TABLE 1

| Substance | Capacitive type |
| --- | --- |
| Humidity | $Al_2O_3$, polyimide, $TiO_2$, $SiO_2$, SiC, polyesters, PMMA (Polymethyl methacrylate), BCB (Benzocyclobutene), polysulfates, cellulose acetate butyrate, porous silicon |
| $CO_2$ | Fluoropolymer, CuO mixed with $BaSnO_3$, $SrTiO_3$, $CaTiO_3$, ZnO or $BaTiO_3$, N—H containing polymers |
| $O_2$ | Zirconium oxide, Irridium oxides |
| Ethylene | $SnO_2$ based film |
| $NH_3$ | Porous SiC, $TiO_2$ |

Further examples of suitable sensitive materials can be found in, for example, Table 2 of "Materials Used as Chemical Sensor Elements" in "Chemical Sensor Technology", Vol. 1, Ed. Tetsuro Seiyama, Elsevier 1988.

Figure 4:
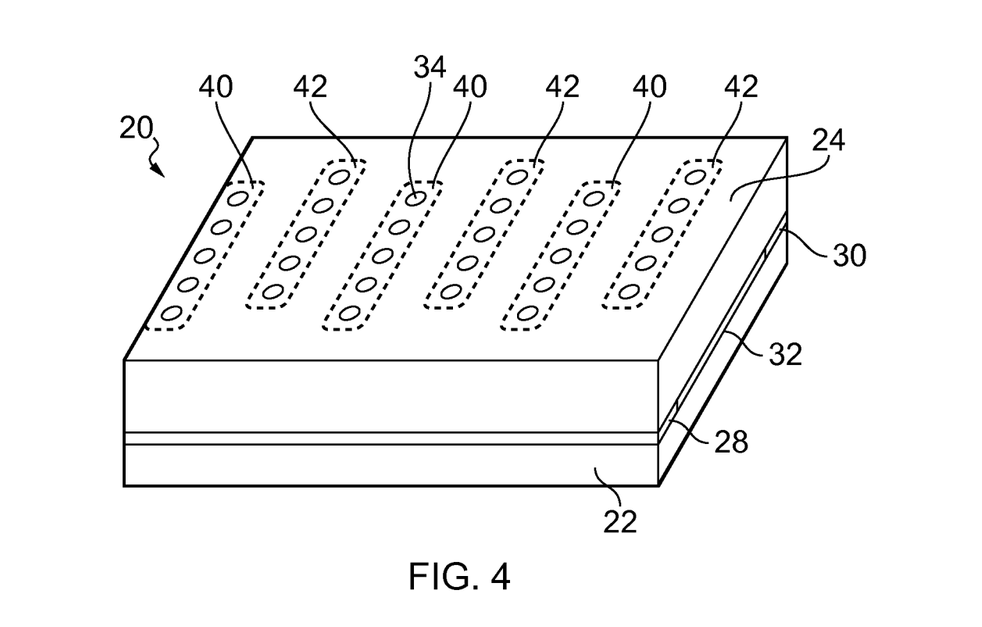

In FIG. 4, the sensor 20 is shown with the dielectric layer 26 removed, to reveal the distribution of the conductive pillars 34 in the pillar layer 24. As can be seen from FIG. 4, in this example, the conductive pillars are arranged into a first group 40 and a second group 42. The conductive pillars of the first group 40 form a first capacitor plate of the sensor 20, while the conductive pillars of the second group 42 form a second capacitor plate of the sensor 20. The first group 40 and the second group 42 of conductive pillars 34 in this example are arranged in alternating rows. A plan view of this configuration can be seen in FIG. 7, which illustrates that at least some of the nearest neighbours of each of the conductive pillars in one of the group comprise conductive pillars from the other group. Thus, in this example, each conductive pillar has four nearest neighbours, two from each group of conductive pillars, and four next nearest neighbours, which are all comprised of conductive pillars from the other group of conductive pillars.

It is envisaged that the conductive pillars in each row may be offset with respect to the conductive pillars of adjacent row, in order to tailor the nearest and next nearest neighbour configurations of each conductive pillar, and thereby to tailor the overall capacitance of the conductive pillars in each respective group. Additional configurations and layouts for the conductive pillars in alternative embodiments will be described in more detail below.

Figure 5:
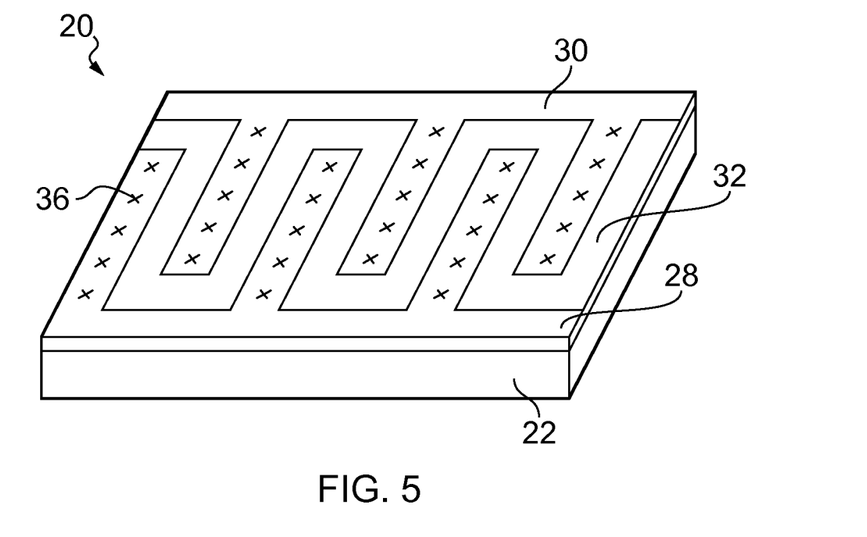

FIG. 5 illustrates the capacitive sensor 20 with both the dielectric layer 26 and the pillar layer 24 removed, in order to reveal the configuration and layout of the first 28 and second 30 electrodes and the dielectric 32 in the electrode layer 31. As can be seen from FIG. 5, the first electrode 28 and the second electrode 30 form a plurality of interdigitated fingers and the dielectric 32, which separates the first electrode 28 from the second electrode 30, thus takes on a meander pattern. The crosses 36 in FIG. 5 illustrate the positions of the pillars in the pillar layer 24, with respect to the electrodes in the electrode layer 31.

Any suitable conductive material can be used to form the first electrode 28 and the second electrode 30, for example Au, Al, Cu, Ti, TiN, Ta, TaN, W, which are standard materials used in used in IC processing. It is envisaged that non-standard materials such as Pt or Ag may also be used.

In this example, the first electrode 28 and the second electrode 30 are provided in a common layer (the electrode layer 31). However, as described below, it is envisaged that the first electrode 28 and the second electrode 30 may be provided in separate layers. Typically, these separate layers may nevertheless be provided on the same side of the pillar layer 24, so that the opposite side of the pillar layer 24 is free to accommodate the dielectric layer 26. The meander pattern of the dielectric 32 can also be seen in FIG. 7.

Figure 6:
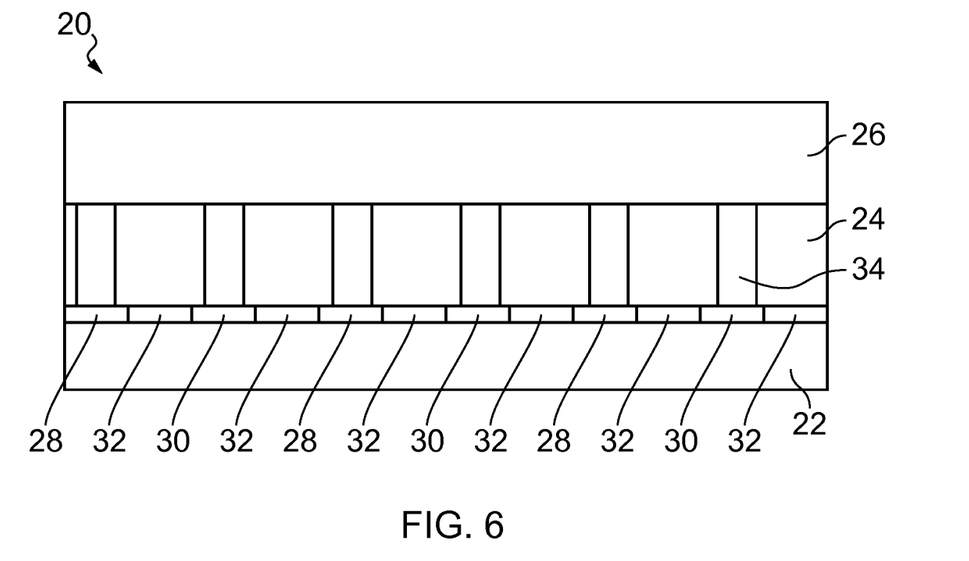
Figure 7:
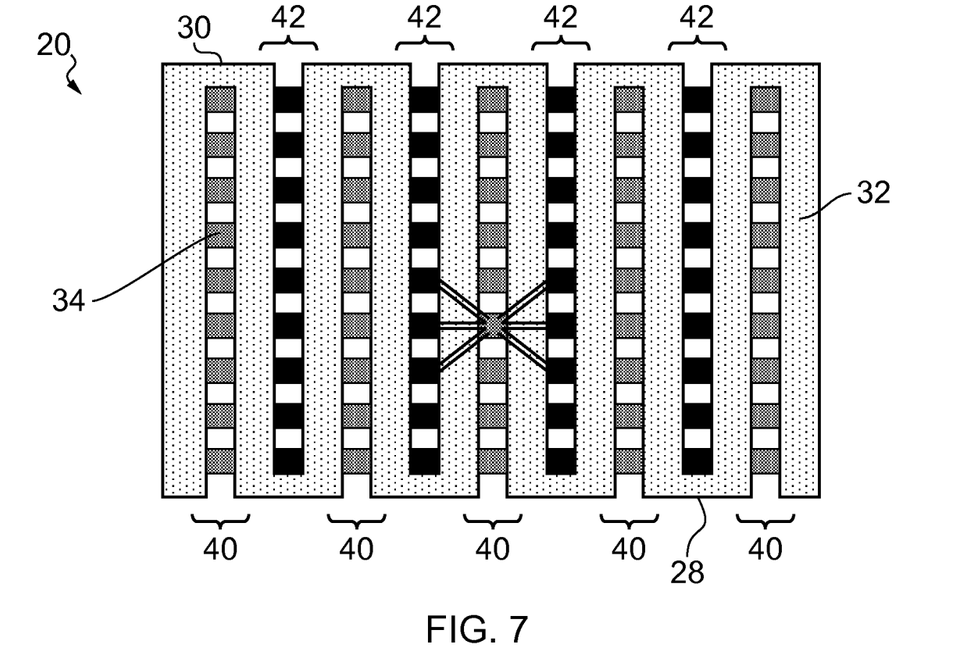

FIG. 6 is a cross-section view of the sensor 20, through the line AA in FIG. 3. Thus, FIG. 6 illustrates the alternating configuration of the fingers of the first electrode 28 with the fingers of the second electrode 30, interspersed with the meander pattern of the dielectric 32. It is thus the layout of the first electrode 28 and the second electrode 30 in the electrode layer 31, which determines the alternating configuration of the rows of conductive pillars 34 in the pillar layer 24.

To produce a sensor 20 of the kind shown in FIGS. 3-7, standard semiconductor processing techniques can be employed. For example, the conductive pillars can be produced using known techniques for providing vias. Therefore, to produce the pillar layer 24, standard techniques can be used, and it is merely necessary to determine in advance the desired arrangement and configuration for the layout of the groups of pillars. The pillars themselves can, for example, comprise tungsten plugs, which is a standard metal used for interconnect via processing in semiconducting processing.

Standard processing techniques can also be employed to produced the electrode layer 31 (for example, damascene processing may be used). The dielectric 26 can also be deposited over the pillar layer 24, using standard deposition techniques, following the laying down of the electrode layer 31 and the pillar layer 24.

Figure 8:
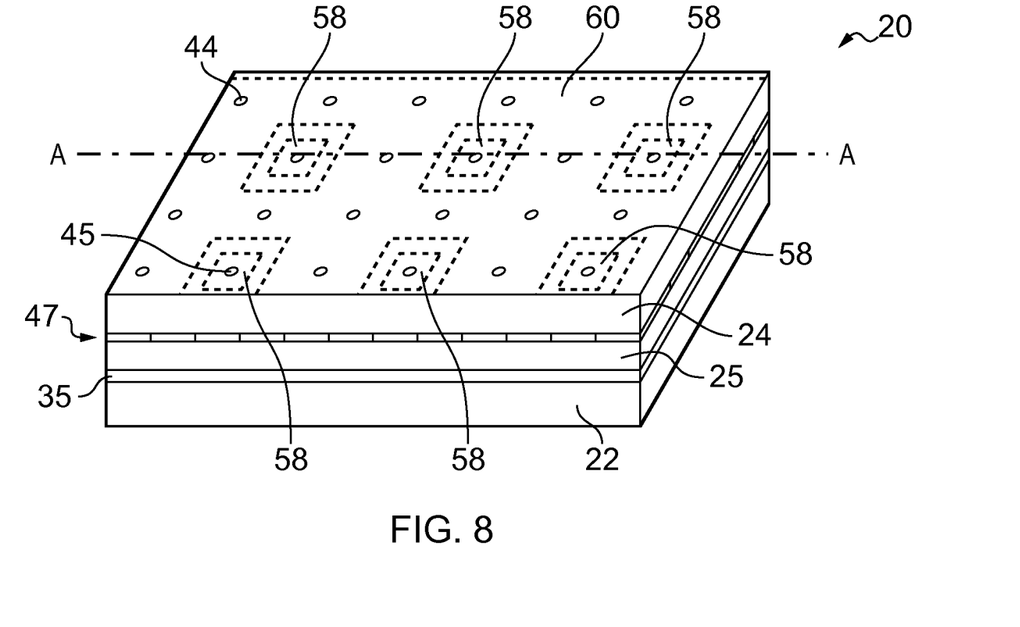
FIGS. 8-11 schematically illustrate a capacitive sensor according to another embodiment of the invention.

A second embodiment of the invention is shown in FIGS. 8-11. Although not shown in FIGS. 8-11, it is envisaged that this second embodiment will also be provided with a dielectric layer 26 of the kind discussed above in relation to FIG. 3. This dielectric layer would be provided adjacent the pillar layer 24, in common with the configuration shown in the first embodiment. FIG. 8 thus shows a capacitive sensor 20 in which the dielectric layer 26 has been removed to reveal the pillar layer 24.

As described in relation to the first embodiment, the pillar layer 24 includes a plurality of pillars 44, 45 interspersed with a dielectric material. Also as described above, the pillars may, for example, comprise a series of vias provided in the substrate 22 of the sensor 20. As can be seen from FIG. 8, the arrangement of the pillars in this example differs from the arrangement of the pillars in the first embodiment. In particular, in this example, the pillars 45 in a first group 58 are provided in a square array and are surrounded by pillars 44 of the second group 60 of pillars. The pillars of the second group 60 are also laid out in a square array, with a pillar 44 provided at the corner of each square, and additionally, in this example, with a further pillar at an intermediate position, between the corners of each square (on the face of each square). This configuration ensures that all of the nearest neighbours and all of the next nearest neighbours of each conductive pillar 45 in the first group 58 comprise conductive pillars 44 of the second group 60. In other examples, by emitting the further pillars of the second group which are provided on the faces of each square, a configuration would be reached where all of the nearest neighbours of each pillar 45 in the first group 58 would be pillars 44 of the second group 60, but where the next nearest neighbours of the pillars 45 in the first group 58 would also comprise pillars 45 from the first group 58.

As will be described in more detail below, this kind of configuration, where the pillars of one group substantially surround the pillars of another group can be employed in configurations other than those shown in FIG. 8. Thus, arrays other than square arrays could be employed. This kind of configuration improves the capacitance of the groups of conductive pillars, since (at least) all of the nearest neighbours of the conductive pillars in one group comprise conductive pillars from the other group. This close proximity of the pillars from one group to a plurality of pillars in the second group ensures a small mean-spacing between the pillars of the two groups, which leads to an increase in the capacitance of the first group with respect to the second group.

Figure 9:
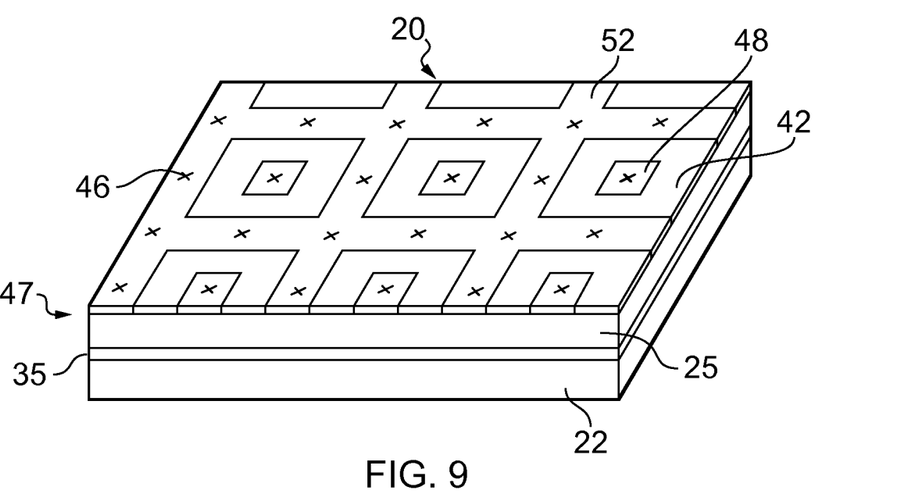

FIG. 9 illustrates the capacitive sensor 20 of this example with the pillar layer 24 removed to reveal the electrode layer 47. As with FIG. 5 above, the crosses 46 in FIG. 9 illustrate the positions of the conductive pillars in the pillar layer 24 with respect to the electrode layer 47. As will be described in more detail below, in this example, the first electrode 50 of the sensor 20 and the second electrode 52 of the sensor 20 in this example are provided in separate layers. The layout of the second electrode 52 within the electrode layer 47 is shown in FIG. 9. In common with the first embodiment, the layout of the second electrode 52 in this example is substantially defined by the layout of the dielectric 42. As can be seen from FIG. 9, the layout of the second electrode 52 is substantially in the form of a square array. As will be described in more detail below, other layouts are envisaged, for example, hexagonal.

In this example, the electrode layer 47 further includes dummy electrodes 48, which correspond to the conductive pillars 45 of the first group 58. These dummy electrodes 48 connect to the conductive vias 45 of the first group 58 and also connect to further conductive vias provided in a further via layer 25, thereby in turn to connect to the first electrode 50 which is provided in the further electrode layer 35.

Figure 10:
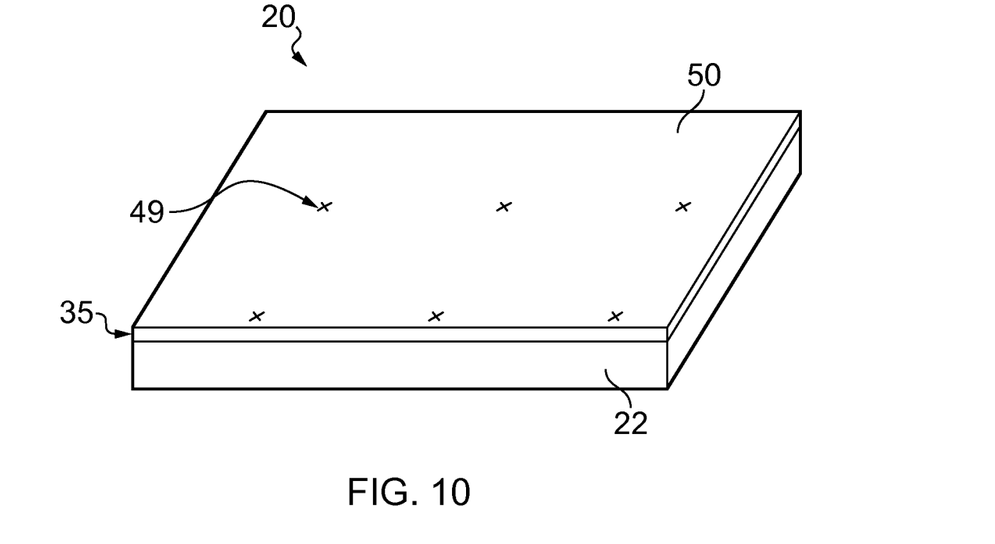

FIG. 10 shows the capacitive sensor with the dielectric layer 26, the pillar layer 24, the electrode layer 47 and the further pillar layer 25 removed, thereby to reveal the further electrode layer 35. The further electrode layer 35 accommodates the first electrode 50, which connects to the conductive vias 45 of the first group 58 via further conductive vias provided in the further via layer 25, and the dummy electrodes 48 provided in the first electrode layer 47. The positions of the conductive vias 45 of the first group 58 with respect to the first electrode 50 are shown in FIG. 10 by the crosses labelled 49.

In this example, the first electrode 50 is shown as comprising a solid unpatterned electrode. However, it is envisaged that the electrode 50 may be patterned in some way, with features which extend to connect with the pillars of the further pillar layer 25 at the positions marked by the crosses 49.

By providing the first electrode 50 and the second electrode 52 in separate layers, greater flexibility is afforded for determining the configuration and layout of the first group of conductive vias with respect to the second group of conductive vias. For example, it is clear from FIGS. 8 and 9 that is would not be possible to make electrical connections to the dummy electrodes 48 within the first electrode layer 47, without greatly complicating the layout of the first electrode layer 47. These complications would further result in the necessity for a substantial reduction in the minimum feature size in the first electrode layer 47. Thus, in accordance with this embodiment of the invention, the connections to the first conductive pillars 45 are provided separately, whereby the layout of the two electrode layers is substantially simplified.

Figure 11:
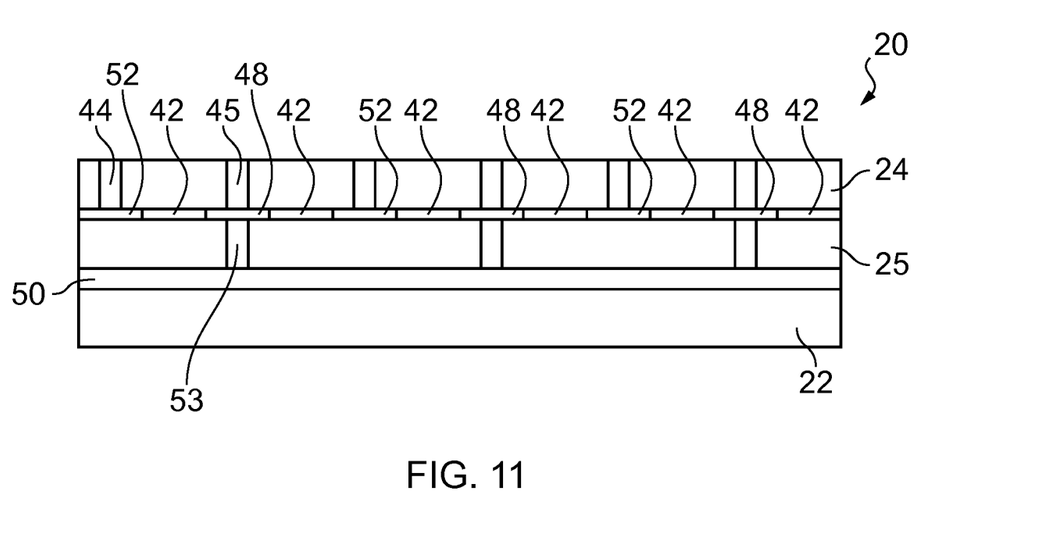

FIG. 11 illustrates a cross-section of the capacitive sensor 20 through the line AA in FIG. 8. FIG. 11 illustrates the configuration of the conductive pillars 44 of the second group 60, which connect to the second electrode 52 in the first electrode layer 47. FIG. 11 also shows the configuration of the conductive vias 45 of the first group 58 and their connection to the dummy electrodes 48 in the first electrode layer 47. FIG. 11 further shows how the dummy electrodes 48 connect with the first electrode 50 in the electrode layer 35 via the further vias 53 in the further via layer 25 of the sensor 20.

As indicated above, the provision of the first and second electrodes in separate layers affords greater flexibility with respect to the layout of the conductive vias to which those first and second electrodes connect. A number of different examples of layouts for the conductive vias of the first and second groups in accordance with different embodiments of this invention will now be described in relation to FIGS. 12-14.

Figure 12:
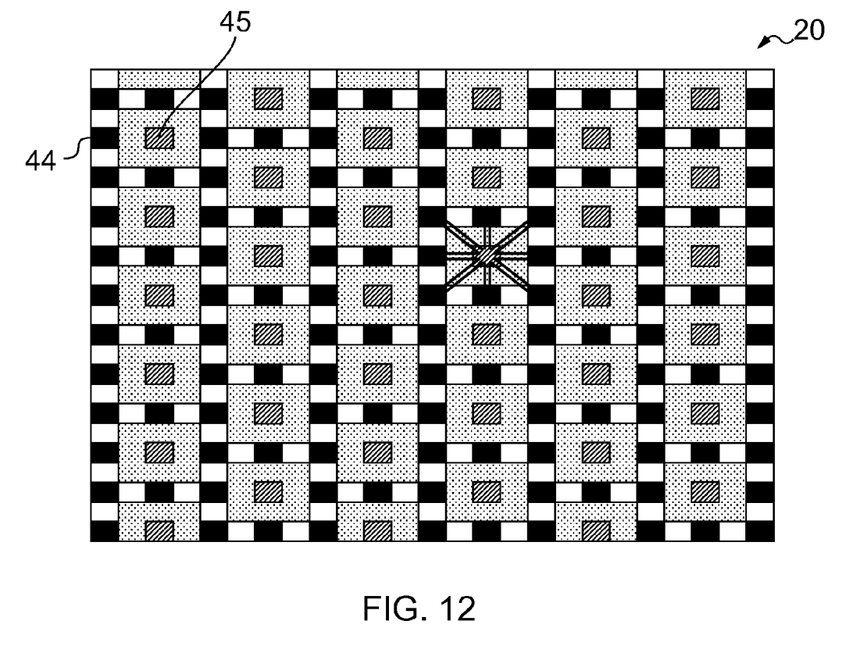
FIG. 12-14 schematically illustrate alternative layouts for a capacitive sensor according to an embodiment of the invention.

In FIG. 12, an arrangement is illustrated which is similar to that described above in relation to FIG. 8. However, in FIG. 12, adjacent rows of conductive pillars 45 of the first group are slightly offset with respect to each other, such that the pillars of the first group are arranged in an array of tessellating parallelograms. The conductive pillars 44 in the second group are also offset, such that all of the nearest neighbours of the conductive pillars 45 in the first group comprise conductive pillars 44 from the second group. Additionally, all of the next nearest neighbours of the conductive pillars 45 in the first group comprise conductive pillars 44 from the second group. The offsetting of the conductive pillars 45 in adjacent rows causes the next next nearest neighbours of each pillar in the first group 45 to comprise conductive pillars in the second group. In contrast, in the example of FIG. 8, the next next nearest neighbours of the conductive pillars in the first group 45 comprise conductive pillars 45 from the same (first) group.

Figure 13:
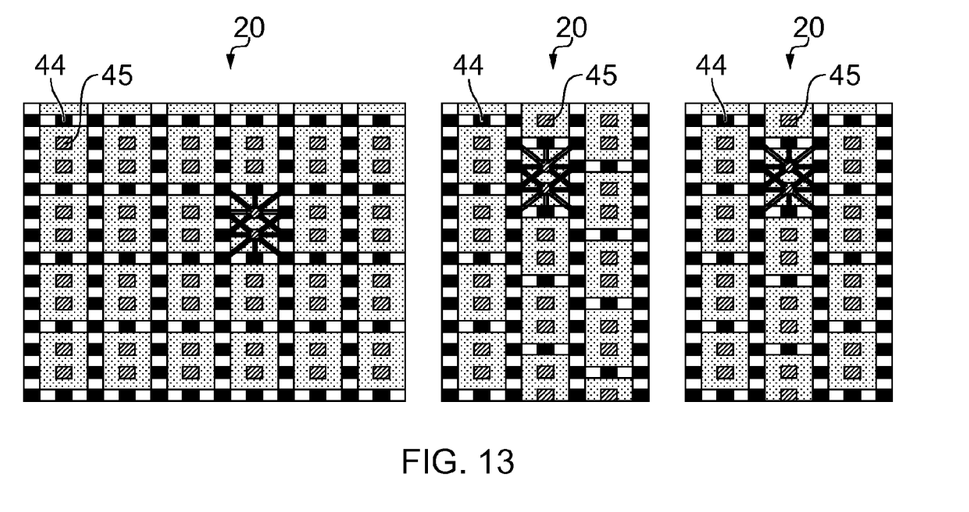

FIG. 13 illustrates a number of further examples in which pillars 45 from the first group are substantially surrounded by pillars 44 of the second group. However, unlike the examples described above, the pillars 45 of the first group are arranged into clusters, where each cluster of pillars 45 is surrounded in a parametric fashion by pillars of the second group 44. Thus, in each of the examples shown in FIG. 13, each cluster comprises two pillars 45 from the first group, and each cluster is surrounded by pillars 44 from the second group arranged in a substantially rectangular array, with a pillar 44 provided at the corner of each rectangle and one or more pillars 44 from the second group further provided along the edges of each rectangle. As shown in FIG. 13, the rectangles can be offset from each other in a manner similar to that described above in relation to FIG. 12, in order to adjust the relative positions of the neighbouring pillars in the overall array.

Figure 14:
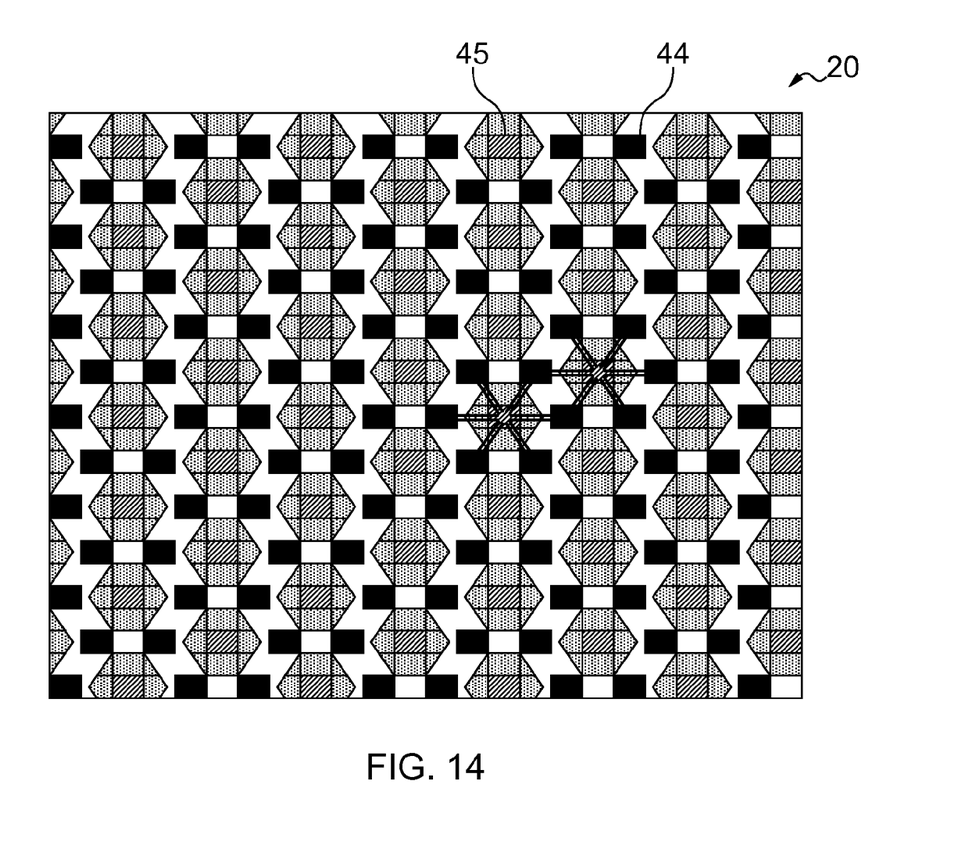

FIG. 14 shows an example in which a non-square array is used. In this example, the pillars 44 of the second group are arranged in a hexagonal array, with a pillar 44 positioned at each of the six corners of each hexagon. It is envisaged that further pillars 44 of the second group could be arranged along the edges of each hexagon in a manner similar to that described above in relation to FIGS. 12 and 13. The pillars 45 of the first group in the example shown in FIG. 14 are provided at the centre of each hexagon in the array. A hexagonal array allows a configuration in which a maximum number of nearest neighbours comprising pillars of the second group are arranged adjacent the pillars of the first group. Thus, in the example of FIG. 14, the pillars of the first group 45 each have six nearest neighbours comprising pillars 44 of the second group, which constitutes a highly efficient arrangement of the pillars in the two groups, for maximising the effective capacitance of the capacitive sensor 20. In common with the examples described above in relation to FIG. 13, it is envisaged that a cluster of pillars 45 from the first group could be provided at the centre of each hexagon in the array.

Each of the examples described above in relation to FIGS. 12-14 could be constructed using a configuration of electrode layers substantially as described above in relation to FIG. 8-11. In particular, to simplify the connections to the various pillars in the two groups of pillars, the first electrode and the second electrode of the capacitive sensor 20 can be provided in separate layers and connected to the conductive pillars of the two groups, via a series of vias and dummy electrodes.

Accordingly, there has been described a capacitive sensor including a plurality of upstanding conductive pillars arranged within a first layer of the sensor, a first electrode connected to a first group of the pillars, a second electrode connected to a second, different group of the pillars, and a gas sensitive material arranged adjacent the pillars, for altering the capacitance of the sensor in response to the presence of a gas.

Although particular embodiments of the invention have been described, it will be appreciated that many modifications/additions and/or substitutions may be made within the scope of the claimed invention.

The invention claimed is:

1. A capacitive sensor for detecting the presence of a substance, the sensor comprising:
 a plurality of upstanding conductive pillars arranged within a first layer of the sensor;
 a first capacitive structure including at least a part of each pillar in a first group of at least two of said pillars;
 a second capacitive structure including at least a part of each pillar in a second, different group of at least two of said pillars;
 a first electrode connected to the first capacitive structure;
 a second electrode connected to the second capacitive structure; and
 a dielectric material between each of the conductive pillars and configured and arranged to indicate the presence of the substance by altering the capacitance between the first and second capacitive structures in response to the presence of said substance.

2. The sensor of claim 1, wherein the conductive pillars comprise a plurality of laterally adjacent vias in a common layer of a semiconductor substrate, filled with a conductive material.

3. The sensor of claim 1, wherein the dielectric material is located in a second layer of the sensor.

4. The sensor of claim 3, wherein the second layer is adjacent the first layer.

5. The sensor of claim 1, comprising a dielectric material located between the pillars in the first layer.

6. The sensor of claim 1, wherein the first electrode and the second electrode occupy separate layers in the sensor, and wherein the conductive pillars are configured and arranged to have the same size and shape.

7. The sensor of claim 1, wherein the first group and the second group of pillars are arranged in rows.

8. The sensor of claim 7, wherein the rows of the first group of pillars are interdigitated with the rows of the second group of pillars.

9. The sensor of claim 8, wherein the pillars in each row are offset with respect to the pillars in adjacent rows.

10. The sensor of claim 1, wherein the pillars are arranged in a regular array of tessellating polygons, with a pillar from the second group located at corners of each polygon, and with at least one pillar of the first group located toward a center of each polygon.

11. The sensor of claim 10, wherein regular array of tessellating polygons comprises a hexagonal array, with a pillar from the second group located at the corners of each hexagon, and with at least one pillar of the first group located toward the center of each hexagon.

12. The sensor of claim 10, wherein regular array of tessellating polygons comprises a rectangular array, with a pillar from the second group located at least at the corners of each rectangle, and with at least one pillar of the first group located toward the center of each rectangle.

13. The sensor of claim 1, wherein nearest neighbors of the pillars in the first group each comprise pillars in the second group.

14. The sensor of claim 13, wherein next nearest neighbors of the pillars in the first group also each comprise pillars in the second group.

15. A radio frequency identification (RFID) tag comprising the sensor of claim 1.

16. The sensor of claim 1, wherein the conductive pillars are configured and arranged to have the same size and shape.

17. The sensor of claim 1, wherein the first capacitive structure and the second capacitive structure form a capacitor.

18. The sensor of claim 1, wherein the first capacitive structure and the second capacitive structure form a capacitor, and wherein the conductive pillars are configured and arranged to have the same size and shape.

19. The sensor of claim 1, wherein the first capacitive structure and the second capacitive structure form a capacitor, wherein the conductive pillars are configured and arranged to have the same size and shape, and wherein the conductive pillars comprise a plurality of laterally adjacent vias in a common layer of a semiconductor substrate, filled with a conductive material.

20. The sensor of claim 1, wherein the first capacitive structure and the second capacitive structure form a capacitor, wherein the conductive pillars are configured and arranged to have the same size and shape, wherein the conductive pillars comprise a plurality of laterally adjacent vias in a common layer of a semiconductor substrate, filled with a conductive material, and wherein the dielectric material is located in a second layer of the sensor.

* * * * *